(12) United States Patent
Ertl et al.

(10) Patent No.: US 9,025,164 B2
(45) Date of Patent: May 5, 2015

(54) METHOD FOR ASCERTAINING MATERIAL CHARACTERISTICS OF AN OBJECT

(75) Inventors: Thomas Ertl, Florstadt (DE); Raimund Hibst, Erbach (DE); Karl Stock, Eilwangen (DE); Rainer Graser, Ulm (DE); Michael Zint, Ulm (DE)

(73) Assignee: Degudent GmbH, Hanau (DE)

( * ) Notice: Subject to any disclaimer, the term of this patent is extended or adjusted under 35 U.S.C. 154(b) by 223 days.

(21) Appl. No.: 13/637,445

(22) PCT Filed: Mar. 28, 2011

(86) PCT No.: PCT/EP2011/054738
§ 371 (c)(1),
(2), (4) Date: Nov. 5, 2012

(87) PCT Pub. No.: WO2011/117420
PCT Pub. Date: Sep. 29, 2011

(65) Prior Publication Data
US 2013/0050711 A1 Feb. 28, 2013

(30) Foreign Application Priority Data

Mar. 26, 2010 (DE) .......................... 10 2010 016 174
May 11, 2010 (DE) .......................... 10 2010 016 904
Jul. 16, 2010 (DE) .......................... 10 2010 036 447

(51) Int. Cl.
*G01B 11/30* (2006.01)
*G01N 21/25* (2006.01)
(Continued)

(52) U.S. Cl.
CPC ................ *G01N 21/25* (2013.01); *A61C 19/00* (2013.01); *G01B 11/24* (2013.01); *G01B 2210/50* (2013.01); *G01N 21/49* (2013.01); *G02B 21/006* (2013.01); *G02B 21/0064* (2013.01)

(58) Field of Classification Search
CPC ........................... G01B 2210/50; G01B 11/24
USPC ........... 356/73, 601, 609, 612, 402, 128, 154; 433/38–70, 213–215
See application file for complete search history.

(56) References Cited

U.S. PATENT DOCUMENTS 4,893,008 A * 1/1990 Horikawa ...................... 250/234
5,004,929 A * 4/1991 Kakinoki et al. ........ 250/559.06
(Continued)

FOREIGN PATENT DOCUMENTS

CA 2682297 A1 10/2008
CN 101622566 A 1/2010
(Continued)

OTHER PUBLICATIONS

Chinese Search Report dated May 26, 2014, corresponding to Chinese Patent Application PCT/EP2013/053515.
(Continued)

*Primary Examiner* — Kara E Geisel
*Assistant Examiner* — Maurice Smith
(74) *Attorney, Agent, or Firm* — Ladas & Parry LLP (57) ABSTRACT

The invention relates to a method for ascertaining material characteristics of an object, in particular optical properties of preferably semi-transparent objects. The aim of the invention is to obtain material characteristics without complex measuring methods. This is achieved in that spectrally resolved data from measured data of the object are calculated with spectrally resolved data of a reference body in order to ascertain the material characteristics, the measured data being ascertained with a confocal 3D measuring system.

11 Claims, 6 Drawing Sheets

(51) Int. Cl.
*A61C 19/00* (2006.01)
*G01B 11/24* (2006.01)
*G01N 21/49* (2006.01)
*G02B 21/00* (2006.01)

(56) References Cited

U.S. PATENT DOCUMENTS

| | | | | |
|---|---|---|---|---|
| 5,835,220 | A * | 11/1998 | Kazama et al. | 356/369 |
| 6,449,087 | B2 * | 9/2002 | Ogino | 359/383 |
| 6,665,557 | B1 * | 12/2003 | Alfano et al. | 600/473 |
| 7,582,855 | B2 * | 9/2009 | Pfeiffer | 250/201.3 |
| 2002/0089667 | A1 | 7/2002 | Kellerhals | |
| 2003/0055435 | A1 * | 3/2003 | Barrick | 606/102 |
| 2007/0280529 | A1 * | 12/2007 | Kaneko et al. | 382/154 |
| 2009/0021750 | A1 | 1/2009 | Korner et al. | |
| 2010/0033719 | A1 | 2/2010 | Hendriks et al. | |
| 2010/0099984 | A1 | 4/2010 | Graser | |

FOREIGN PATENT DOCUMENTS

| | | |
|---|---|---|
| DE | 10 2006 007 172 | 8/2007 |
| WO | WO 2005/068953 | 7/2005 |
| WO | 2008104913 A1 | 9/2008 |

OTHER PUBLICATIONS

Chinese Search Report dated May 26, 2014, corresponding to Chinese Patent Application 201180016233.5; with English Translation attached.

* cited by examiner

METHOD FOR ASCERTAINING MATERIAL CHARACTERISTICS OF AN OBJECT

This application is a 371 of PCT/EP2011/054738, filed on Mar. 28, 2011, which claims priority to German patent application number 10 2010 016 174.8, filed Mar. 26, 2010, German patent application number 10 2010 016 904.8, filed May 11, 2010, and German patent application number 10 2010 036 447.9, filed Jul. 16, 2010.

The invention relates to a method to determine the material characteristics of an object.

During the optical scanning of three-dimensional objects it may be practical for several reasons to have knowledge of the material properties, in particular the optical characteristics of the region to be measured. This applies to both the surface data and the volume material characteristics in the case of semi-transparent objects.

For example, for objects composed of different materials it may be practical to display these materials differently in the 3D data set as well, or for the purpose of applying material-independent filter algorithms. It is also possible to apply special filters (or algorithms for data processing) selectively to material border regions within an object to be scanned, if the position of the line of separation is known.

Furthermore, for geometrically non-variant objects embedded in surroundings with variable geometry it may be practical to separate the objects by means of their different optical properties, in as far as these exist.

In addition to using the material characteristics for the 3D reconstruction, the determination of material characteristics for example can also be helpful for representing the material compartments or in the dental region for detecting tooth decay, inflammation, or the condition (colour, degree of polymerization) of composite fillings.

Known from DE-A-10 2007 019 267 is a 3D measurement of an object, in particular a semitransparent object, by means of a chromatically dispersing confocal technique. The measured spectral data are used to determine the Z coordinates of a multitude of test points. Accordingly, the determination of the Z coordinate takes place independent of material. Also known are the spectral diffuse reflection data and optical properties of various materials (WO-A-2005/068953).

US-A-2010/0033719 relates to a method and an apparatus to ascertain the optical characteristics of textile fabrics. For this, spectral recordings are obtained point-by-point by confocal spectroscopy from different regions of the fabric, in order to be able to obtain information about the reflection and absorption properties of the fabric.

Subject matter of DE-A-10 2006 007 172 are a method and an arrangement for the rapid, spatially resolved, two-dimensional spectroscopic analysis of an object. For this one uses a grid surface array of pinholes.

Objective of the present invention is to provide a method to ascertain material characteristics, in particular optical properties of objects, preferably in the dental region, without requiring complicated measuring procedures. The measuring instruments should be of a simple design to allow high ease of use.

To meet this objective the invention fundamentally intends that for the purpose of ascertaining optical properties as the material characteristics of the object, spectrally resolved data from measured data of the object obtained with a confocal 3D measuring system are balanced against spectrally resolved data of a reference body, whereby one determines several sets of spectrally resolved data of test points at varying distance of the measuring system from the object, and that applied to the measured, spectrally resolved data is a correction factor that is determined from spectra of the reference body, the reflection of which is measured not under confocal measuring conditions or the spectra of which are retrieved from a library stored in the computer.

The confocal 3D measuring system in particular is a confocal colour-dispersing 3D measuring system, such as it is described in DE-A-10 2007 019 267, whereby this publication's disclosure is expressly and completely referenced.

As reference body one in particular uses a reference body made from a highly diffusely scattering material, such as titanium dioxide or Spectralon.

In accordance with the invention, one uses the data of each test point, spectrally dispersed in accordance with the optical principle of a 3D scanner, in order to use the gained information for the purpose of characterizing and differentiating the materials, provided that the materials are different with respect to their optical properties, such as refraction index anisotropy factor, scattering and absorption coefficient, or fluorescence.

In accordance with DE-A-10 2007 019 267 one uses for this purpose at least one light source, in particular a light source emitting a continuous spectrum, a device to generate a multi-focal illumination pattern, an objective lens with large chromatic aberration to image the foci of the illumination patterns onto the object, a detector device to determine the wavelength spectrum of the foci imaged onto the objective lens of the object, whereby for each respective wavelength spectrum the spectral peak position is determined for each focus, from which one then computes the extent of the object along the direction of the imaging ray (Z coordinate). Arranged in the plane, in which the foci are confocally imaged by the objective lens, is a first hole pattern with first holes, whereby their geometrical pattern correlates with that of the multi-focal illumination pattern.

The positions of the first holes predetermine the positions of the foci on the object to be in a plane (X, Y coordinates) extending perpendicular relative to the imaging ray, whereby the wavelength spectra of the foci imaged in the holes are detected by the detecting device. For this, the wavelength spectrum of each focus imaged in a hole is laterally dispersed by a dispersing device arranged downstream in the beam path. In addition, second holes are associated with the first holes of the hole pattern, whereby the positioning of the second holes deviates from the multi-focal illumination pattern. Consequently the second holes receive diffuse reflected signals, since the foci are not imaged onto the second holes by the objective lens. Consequently one may use as a measuring method both the direct back reflection in the test point (including Fresnel component for suitable angles), which in the case of a semitransparent object will be superimposed onto a diffuse back reflection signal from the close vicinity of the test point within the measuring aperture, as well as the observation of the backscattered signal spatially offset by a small distance in the range of for example 5 μm to 3 mm, preferably 10 μm to 200 μm, or the combination of both signals.

The direct back reflection, i.e. the diffusely reflected radiation from one of the imaged foci, may in particular be used to infer information about the degree of roughness, i.e. the property causing diffuse scattered reflection, of the material; since strong Fresnel reflections are only detected in areas of low roughness. Spectra obtained from the not illuminated points are then used to obtain information on subsurface scattering.

Because of the confocal condition and the colour-dispersing lens a different narrow wavelength region dominates at each Z depth. Other wavelength regions are suppressed. If the Z depth of the 3D measurement is known, this effect can be compensated for in a re-computation, since the characteristics of the confocal lens are known. However, this property, which is essential for the depth measurement, will in the assessment of the material characteristics result in a deterioration of the signal/noise ratio in the suppressed wavelength regions, i.e. to a reduction of the usable spectral region.

For this reason, the invention proposes to determine several spectra for the same test point, but with different distances between the measuring device and the object, in order to subsequently weight the spectra, i.e. to compute their mean value. This allows improving the unfavourable signal-to-noise ratio.

It should also be taken into consideration that certain characteristic features in the spectrum, such as for example a skewness of the peak can be caused by influences different from the material characteristics, e.g. by an oblique positioning of the surface. This should be subjected to a separate evaluation, in order to prevent erroneous conclusions about the material characteristics to be determined.

In a further mentionable embodiment of the invention it is intended that an additional optical, non-confocal measurement be performed to determine the material characteristics. In the prior art device published in DE-A-10 2007 019 267 this may be achieved using the means that facilitate the generation of a live image.

In the presence of one or several additive, non-confocal reference channel(s), for example for realizing a live image during the 3D measurement, this/these channel(s) may also be used in the determination of the material from the optical properties.

The full-area illumination of the test object can be achieved by one or several additional light source(s). If the wavelength range of the additional light source(s) is outside of the wavelength region of the 3D measuring system, the two measuring systems will be essentially independent. Alternatively, the two systems may perform measurements in an alternating fashion. The use of more than one wavelength in the reference channel preferably is realized by a time-staggered alternating activation of various LEDs or laser diodes. The light source clocking is synchronized to the frame repeat rate of the measuring sensor. In the case of two light sources, every second image will be illuminated by the same light source.

As sensor one uses either—in particular for sequential illumination from several light sources—a monochromatic sensor, or a colour sensor, e.g. an RGB chip. Also feasible are several monochromatic sensors in combination with suitable colour splitters.

The additional imaging sensor can either be positioned with its own lens upstream of the chromatic objective lens (using beam decoupling), or may be positioned downstream of the latter, using a chromatic objective lens for imaging. Also feasible is a second measurement with its own optical imaging, which is not coaxial with that of the chromatic objective lens.

If the chromatic lens is used for imaging, one can either position the colour sensor so that one wavelength is imaged in focus and provides the structural resolution. The other wavelengths provide spectral information, however with reduced spatial resolution. Or it is possible to use several monochromatic sensors in combination with suitable dichroic filters, whereby preferably—corresponding to the dispersion of the chromatic objective lens—the individual axial positions of the sensor are matched to the respective imaging planes.

Alternatively one can use a monochromatic sensor with a higher frame rate. For example, three LEDs may be synchronized to the frame rate. The first image will provide the structural resolution in a sharp picture, while the following images contribute to the colour determination. The final resolution is limited by the least sharp image. The effective, adjustable frame rate is reduced by the number of colour channels, according to the relation: effective frame rate=frame rate/number of colour channels.

Depending on the particular application, one may choose a combination of white light source and filter wheel instead of varying the illumination wavelength.

Naturally an evaluation of fluorescence may also be employed if suitable filters are used in the reference channels.

Surface roughness or smoothness of the surface can possibly be determined using several frames, i.e. images, since the Fresnel reflex only becomes relevant if the measured surface and the optical axis of the measuring system are orthogonal, and this condition will only be met sporadically during the scanning. By matching—also referred to as registering—several recordings of the object—preferably one records at 30 frames per second—one unites representations of individual surface points of individual scans on the sensor, whereby the angles of illumination and the point of view will be different since the scanner is being moved. Irrespective thereof, it is possible to assume for each frame that no relative movement exists between the measuring device and the object, since one frame represents a time of approximately 35 ms. If for single frames one observes high brightness fluctuations in at least one test point in a direct back reflection, one can assume a smooth surface in the respective area. Naturally the relative position finding may also be performed by inertial platforms on the sensor and the test object.

In particular it is intended that for ascertaining the spectrally resolved data, the object be illuminated by a first radiation with a wavelength range $\Delta\lambda 1$ by means of the 3D measuring system, that the object be illuminated by a second radiation of a wavelength range $\Delta\lambda 2$, and that a 2D image of the object be determined from the second radiation emitted by the object, whereby in particular $\Delta\lambda 1 \neq \Delta\lambda 2$. In this it is intended that the 3D measuring system contain a first sensor with first pixels to be assigned to spatial coordinates of the object and the 2D image be recorded by means of a second sensor with second pixels to be associated with positional coordinates of the object, and that the first pixels and the second pixels be assigned to each other. This allows a unique assignment between spatial coordinates and material characteristics, whereby information about auto-fluorescence characteristics of the object can be inferred in particular from the returned radiation in the wavelength range $\Delta\lambda 2$.

According to the invention, it is intended that added to the measured spectra is a correction factor, which is determined from the spectra of a reference body, whereby the latter's diffuse reflection is not measured under confocal measuring conditions or that the spectra are taken from a library stored in a computer.

In this it is intended that the measuring spectra are compared—taking into consideration the correction factor—to spectra, which are representative for material characteristics and have been stored in look-up tables.

Preferably it is further implemented that material characteristics are ascertained both from a measured spectrum of a test point determined under confocal conditions as well as from a background spectrum within the vicinity of the test point.

Further details, advantages, and features of the invention are not only found in the claims and the characteristic features described therein—on their own and/or in combination—but also in the following description of preferred embodiment examples described in the figures.

According to the invention, data of each test point out of a multitude of simultaneously recoded test points are used to infer information about the surface geometry of an object, in particular of a semi-transparent object such as a tooth or jaw region, and simultaneously are determined material characteristics of the object, in particular by analysing spectrally resolved data, which provide information on the spatial coordinates of the object. This is achieved by using a device as it is disclosed in DE-A-10 2007 019 267, whereby as mentioned before, the latter's disclosure is expressly referenced. Consequently, the measuring set-up of FIG. 1 corresponds to the one in DE-A-10 2007 019 267.

Figure 1:
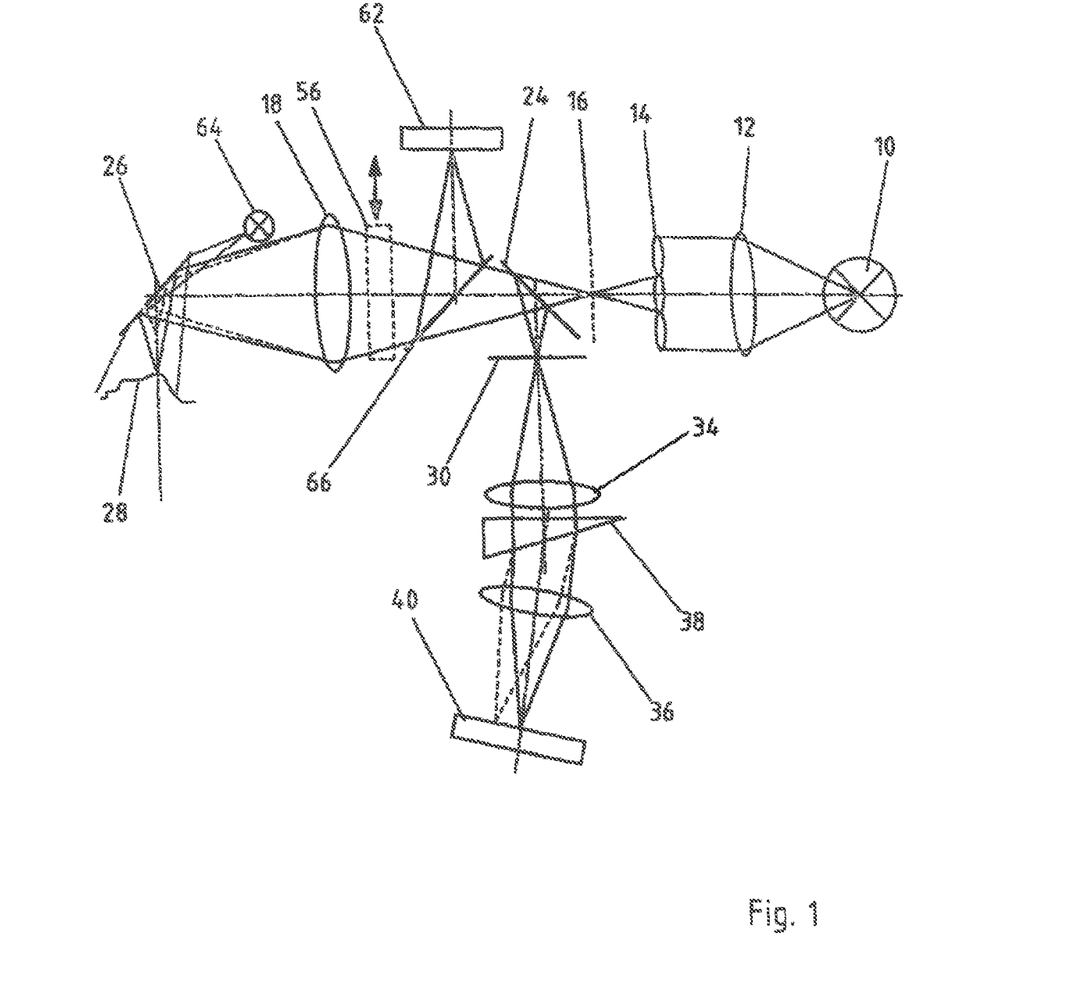
FIG. 1 shows a schematic illustration of a 3D-measuring set-up.

The measuring set-up comprises as fundamental elements a light source 10, such as a halogen lamp, whereby the latter's light is collimated by a lens 12. The collimated light beam is incident upon a micro-lens array 14, which images an illumination pattern 16 in the focus plane of an objective lens 18 with high chromatic aberration.

The illumination pattern generated by the micro lens array 14 may possess a size of, for example, 20 mm by 15 mm with approximately 1600 foci, or for example a size of 5 mm by 6.5 mm with approximately 2000 foci at a separation of 250 μm.

The illumination pattern 16 can be designed in such a way that the diameter of the foci 20, 22 will be approximately 25 μm or approximately 12 μm, respectively.

To improve the illumination pattern, the micro lens array 14 may be combined with a matched pinhole array, which is located in the object plane of the objective lens 18. In this, the holes of the pinhole array are geometrically, i.e. positionally, matched to the illumination pattern formed by the foci.

In accordance with the illustration of FIG. 1, the light originating in the light source 10 is incident—downstream of the illumination pattern 16—upon a beam splitter 24, from which the transmitted portion is incident upon the objective lens 18 with high chromatic aberration.

In the drawing, the beam splitter 24 is represented as a plate with a partially reflecting layer. Other beam-dividing elements are feasible as alternatives. Beam splitter cubes should be mentioned as an example. One can envision annular mirrors or smaller-sized mirrors, whereby the inner or the outer beam component is available for the detection to be explained in the following or for the illumination.

The radiation passing through the objective lens 18 is imaged onto an object to be measured 28, such as a tooth, by a deflecting device 26 such as a deflecting mirror. In this, one chooses the distance between the plane of the illumination pattern 16 and the object 28 in a way so that after being deflected by the deflecting device 26 the foci are imaged onto the surface of the object 28, whereby different colours, i.e. wavelengths will be imaged in focus, depending on the distance of the object surface to the objective lens 18. In this, the chosen imaging scale determines the size of the measuring field and the resolution.

Radiation or light returned from the object 28 in part is incident upon the objective lens 18 again and after partial reflection at the beam splitter 24 reaches a first hole pattern or pinhole array 30, with holes that with respect to hole distance, overall size, and geometrical arrangement match the illumination pattern 16.

In other words, the axial and lateral position of the pinhole array 30 or rather of its holes is chosen so that the foci on the surface of the object 28 are imaged in a confocal manner into the holes of the pinhole array 30. In this way each hole of the pinhole array 30 specifies the X, Y coordinates of the imaged focus on the surface of the object 28.

Figure 2:
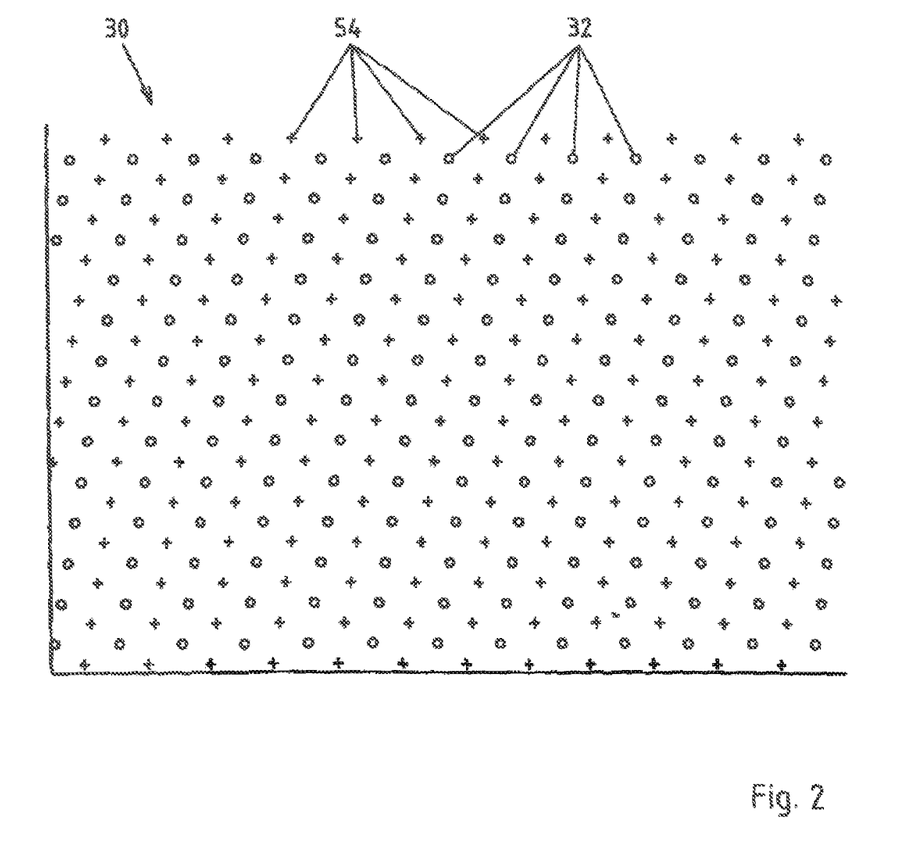
FIG. 2 shows a hole pattern with first and second holes.

FIG. 2 illustrates the pinhole array 30, whereby the open circles 32 with respect to their arrangement and size correspond to the pattern of the foci of the illumination pattern 16.

As a result of the high chromatic aberration of the objective lens 18, only one particular colour will be imaged in focus in any test point predetermined by the position of the foci of the illumination pattern 16, in particular in dependence on the point's distance from the objective lens 18, i.e. only one wavelength satisfies the confocal condition. Correspondingly, the spectrum of the light transmitted through the respective hole 32 of the pinhole array 30 will show an intensity maximum at this wavelength.

With increasing density of the test points and with increasing light output of the object 28, an increasing portion of white light will be passing through the hole or pinhole in addition to the peak wavelength. In order to still be able to determine the peak wavelength characteristic of the particular focus to an adequate degree and with sufficient accuracy, it is intended that arranged downstream of the pinhole array 30 be a spectrometric arrangement matched to the illumination pattern 16 and consequently the hole pattern of the pinhole array 30, which in the embodiment example consists of optical elements 34, 36 and a spectrally dispersing element arranged between them, which in the embodiment example is a prism 38.

Via the optical elements 34, 36, which may consist of one or several lenses, the pinhole array 30 is imaged onto a CCD area sensor that is used as detecting device 40. The spectrally dispersing element, i.e. the prism 38, effects a lateral spectral dispersion of the wavelength region of the focus light that in the holes is causing an intensity maximum, so that consequently each hole of the pinhole array 30 is imaged onto a line on the CCD area sensor 40, i.e. on the pixels arranged on a surface, whereby—as in a line spectrometer—the position along this line correlates with the wavelength. In this, the CCD sensor 40 and the spectrally dispersing unit consisting of the optical elements 34, 36 and the prism 30 is aligned relative to the pinhole array 30 in such a way that laterally dispersed spectral lines from consecutive holes of the pinhole array 30, which form lines on the pixels, will be situated immediately next to each other with no or nearly no empty space in between them, and without any overlap.

If for example one chooses the above-described illumination pattern with the specified dimensions and a CCD chip or camera chip with a size of 6.4 mm×4.8 mm with 1 million pixels (pixel size 6.7 μm by 6.7 μm), one will have 186 pixels available for the spectral dispersion of each test point. With a line width of 2 pixels, corresponding to the pinhole diameter, one will realize in this manner for each of the approximately 2000 test points and approximately 2000 background points a line spectrometer with 93 elements for the spectral dispersion. The recording of the image is followed by a processing of the image information, i.e. the measured data, either directly in the CCD sensor or in an external unit. A suitable algorithm is used to determine for each test point the spectral peak position and from this the distance of each test point to the object 28. With one image one obtains in this manner the three-dimensional structure of the object 28 in the test points or sampling points, whereby the resolution is dependent upon the chosen spacing between the foci and the object-to-image ratio of the objective lens 18.

If the spacing between sampling points is greater than the required resolution and/or if the three-dimensional shape can not be detected from a particular point of view, the illumination pattern 16 can be shifted accordingly.

If the measuring arrangement is a hand-operated device, then a continuous movement of the measuring arrangement can result in a complete sampling of the object 28, whereby the resulting individual images will be merged into a combined image in a suitable manner.

Since—as mentioned before—not only the wavelength of the sharply imaged focus will be imaged in the holes 32 of the pinhole array 30 if the object 28 has highly scattering characteristics, but also to an increasing degree white light, one has to employ procedures to eliminate or reduce the resulting background.

The higher the portion of the white light background in the measured signal is, the more precise one must know for each test point the spectral curve of the background, to be able to determine the position of the peak that is characteristic of the wavelength of the respective focus. For this one may employ a method that is purely schematically illustrated in FIG. 2. In addition to the holes 32 in which the foci are imaged, the pinhole array 30 comprises additional holes 54 that do not coincide with the illumination pattern 14. In accordance with the preferred arrangement of FIG. 2, the holes 54 not coinciding with the illumination pattern 14 are situated between the holes 32 corresponding to the illumination pattern 14. The spectra in the holes 54, in which the foci are not imaged, approximately represent the background signal of the neighbouring holes 32, in which foci are imaged and form test points. In this, it is possible as an alternative method to determine the background 52, to use as background the measured signal of a single neighbouring hole 54 that fundamentally only contains white light or a mean value of several neighbouring holes 54. In this, the holes 54 may be referred to as not illuminated holes whereas the holes 32 may be referred to as illuminated holes or pinholes.

In accordance with the arrangement of the illuminated or first holes 32, in which the foci are imaged, and of the second holes 54 intended for background determination, which also may be referred to as not illuminated holes, one now has available per test point only half the number of pixels for the spectral dispersion, compared to the variant in which the number of foci is identical to the number of pinholes or holes 32.

A live-image acquisition may be provided as positioning aid and for purposes of assigning individual images when creating an overall combined image. For this purpose a further camera chip 62 is provided, onto which the object 28 is imaged. Additionally may be provided a further light source 64, which illuminates the object 28 preferably via the deflection device 26. It is also possible for several light sources to be provided instead of one light source 64. For the live-image recording, the light source 64 should emit light in a spectral region outside the wavelength range used for the actual measurement. This allows performing live image and measurement independently of each other.

For beam-splitting purposes, a second beam splitter 66 may be employed in the beam path between the objective lens 18 and the first beam splitter 24, such as a dichroic filter possessing a high transmission for the measuring signal and a high reflection for the live image signal.

As mentioned above, the objective lens is also used for imaging the object 28 onto the camera chip 62, whereby the axial position of the camera chip 62 is chosen so that the live image will be in focus approximately in the centre of the measuring region.

The dimensions and shape of the measuring arrangement or measuring unit will be of great importance, in particular for an intra-oral application for the measuring of teeth. For example, in a configuration variant of the invention it is possible for only the objective lens 18 and the beam deflector 26 to be arranged in an intra-oral component of a hand-held unit that can be inserted into the oral cavity. The other components may be integrated in an extra-oral part of the hand-held unit or in a separate device unit. Integration into a hand-held unit is possible for compact light sources.

Instead of the halogen lamp 10 one can also envision other light sources, such as for example a white light LED or several different-coloured LEDs with suitable collimation optics.

Alternatively the light source 10 can be integrated into an external unit and the light can be conducted into the hand-held unit via optical fibres, whereby the decoupling end of the optical fibre extends in the focus of the collimating lens 12.

To generate the multi-focal illumination pattern 16, one may use instead of or in addition to the micro-lens array 14 a pinhole array that can be arranged in the plane of the illumination pattern 16 illustrated in the figures.

If the object 28 is not measured, i.e. scanned, by a single recording but by a multitude of recordings, i.e. individual images, the individual images must possess a unique association relative to each other in order to facilitate processing without any complications. For this purpose, it is in particular intended that the images overlap in parts that represent 50% to 95% of each individual image. As an alternative or in addition one may use the introduction of fixed points on the object 28 as an aid for superimposing the individual images.

As an alternative to a manual shifting of the measuring device, which preferably is embodied as a hand-held unit, as mentioned above, positioning actuators may be integrated in the measuring arrangement in order to shift test points. The maximally required shift distance corresponds to the distance between test points minus the desired resolution, i.e. in the explained embodiment example at a desired resolution of 225 μm (250 μm hole separation–25 μm resolution).

Figure 3:
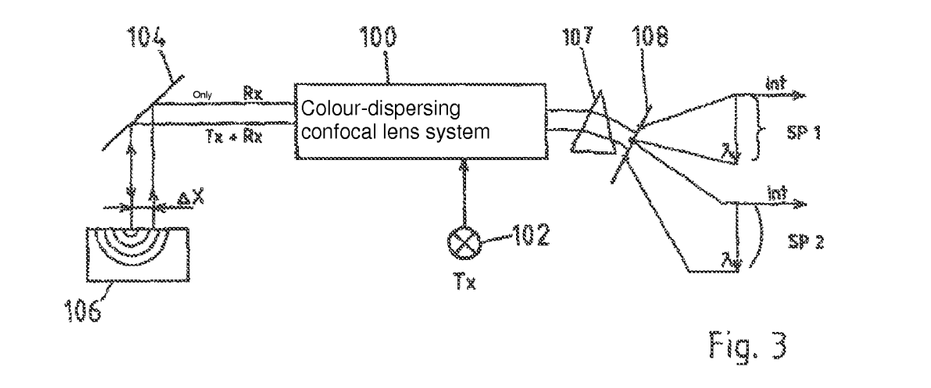
FIG. 3 shows a schematic illustration for ascertaining the material characteristics of an object.

The measuring arrangement schematically explained with the help of FIGS. 1 and 2 is also used to ascertain material characteristics of the object, as is purely schematically illustrated in FIG. 3. For this one uses the confocal system, comprising the illumination pattern 16, the beam splitter 24, the objective lens 18 with high chromatic aberration, as well as the hole pattern 30.

In FIG. 3 the elements are referred to as colour-dispersing confocal lens system 100. The radiation possibly can be generated by a multi-point light source TX102. Arranged downstream of the objective lens 18 may be a deflection element 104 that is used to redirect the radiation onto the object 106, such as a tooth.

In accordance with FIG. 1, arranged downstream of the colour-dispersing confocal lens system 100 is an arrangement 107, such as a prism for spectral dispersion with a sensor 108, on which the spectra of the back-reflected or back-scattered light from the object 106 are presented. In this, one generates spectra SP1 of the directly illuminated test points as well as spectra SP2 on the sensor 108, which are not illuminated by the confocal system 100. The corresponding points are offset by a distance $\Delta x$, which is in a range between 5 μm and 3 mm, in particular in the range between 10 μm and 200 μm. The points of the object 106 that are not illuminated via the confocal system and thus the spectra SP2 are those that are generated by the light, which in the pinhole array 30 passes through the holes 54 used for the background determination.

The spectra SP1 and SP2 subsequently are re-computed using data from a look-up table. To generate the data for the look-up tables, known samples are measured using the system according to the invention and the spectral information SP1, SP2, and possibly additional channels, e.g. the reference channel of the live-image optics, are saved and stored as a data set in the look-up table. Preferably the data are stored in an already z-corrected form. Subsequently the measured data of an unknown material are—also already distance-corrected— compared to the data sets of the look-up table, for example using a best-fit algorithm that calculates least squares for each spectral test point. To calibrate the system, one uses the spectrally resolved data of a reference body made from highly diffusely scattering materials such as titanium oxide or Spectralon, as is explained with the help of FIGS. 6 to 8.

The difference between the corresponding spectra SP1 and SP2 is noticed by the non-presence of the Fresnel reflection in spectrum SP2 and by the higher portion of volume information in the case of a semi-translucent object.

Thus the spectrum SP2 contains more information about deeper regions of the material than the spectrum SP1. However, the spectrum SP2 on its own can also represent a multitude of such corresponding test points.

In contrast, the spectrum SP1 also provides information if the material in question is a material with very low penetration depth, since the return signal from the immediate surroundings is evaluated.

This provides very interesting evaluation options when comparing the two spectra. For example, a smooth metal surface creates a spectrum SP1 of high intensity, for a surface position perpendicular to the line of vision, with Fresnel reflection. In this case, the intensity of the spectrum SP2 is ideally zero.

In the case of a semi-translucent material with a diffusely scattering surface, the spectrum SP1 will predominantly contain information about the material surface, however in this case the spectrum SP2 will not be zero, but will carry information in light scattered by the object, which facilitates the drawing of conclusions about the optical properties of the material. The difference of the spectra SP1-SP2 consequently allows drawing conclusions about the absorption and scattering properties of the material and thus facilitates differentiating between materials.

For smooth material surfaces (e.g. fabrics with liquid films) an occurring Fresnel reflection may present problems. But since these only occur at certain angles of the point of view, the effect can be detected and processed separately, since an occurring of the Fresnel reflection can overload the sensor.

Due to the confocal condition and the colour-dispersing optics, a small wavelength region will dominate for each Z depth while other wavelength regions will be suppressed. If the Z depth of the 3D measurement is known, this effect can be computed out, since the behaviour of the confocal optics is known. However, this property that is essential for measuring the depth, during the assessment of material characteristics will result in a worsening of the signal-to-noise ratio in the suppressed wavelength regions and thus to a restriction of the usable spectral region.

However, this can be compensated for by combining several frames for the same test point, recorded at different distances.

The sensor 108 may be an area sensor or multi-line sensor based on CMOS-, CCD-technology with the materials Si, Ge enhanced Si or InGaAs.

Figure 4:
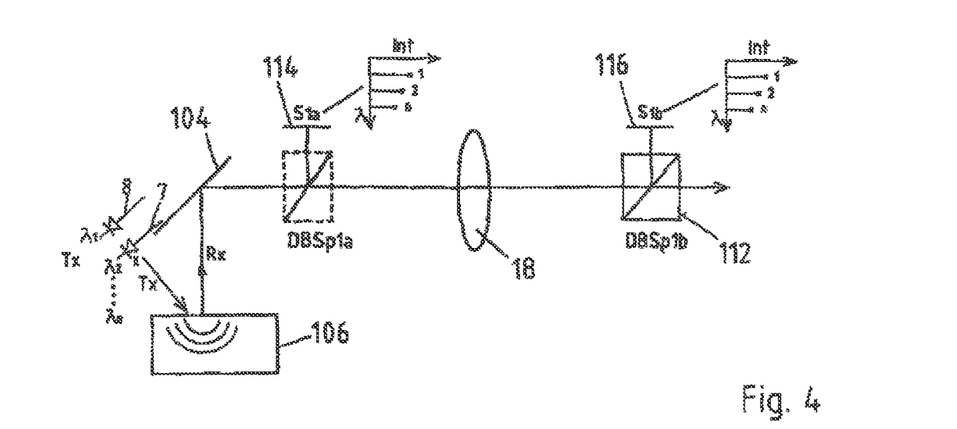
FIG. 4 shows a variation of the set-up of FIG. 1.

FIG. 4 illustrates a preferred further development of the invention's measuring arrangement. Making use of the principle of the live-image generation described in FIG. 1, it is possible to perform a further measurement of the object 106 to determine the material characteristics. From an angle different from the angle of view of the detecting device RX, the object 106 can be illuminated by light sources TX$\lambda$1, $\lambda$2 . . . $\lambda$n using light of a wavelength region $\Delta\lambda$2, which preferably does not coincide with the wavelength region that is used to perform the measurement according of FIG. 3, i.e. the 3D measurement. In this case a dichroic beam splitter 110 or a beam splitter 112 arranged between the objective lens 18 and the beam splitter 24 can be used to direct the wavelengths of interest (n) onto a sensor 114 or 116. This may be the sensor 62 of FIG. 1 used for the generation of the live image. Preferably one uses an arrangement of dichroic beam splitter 110 and sensor 114, since this eliminates the need for the colour-dispersing optic element 18. If several wavelengths $\lambda$1, $\lambda$2 . . . $\lambda$n are used sequentially then a monochrome sensor can be used to record a discrete spectrum DSp3 or DSp4, which contains information about the optical properties of the test object 106, preferably outside of the wavelength region used for the 3D measurement.

The pixels of the sensors 114 to 116 are assigned exactly or nearly exactly to the pixels of the sensor 108, so that for each test point determined in accordance with the arrangement of FIG. 3, information in the extended wavelength region can be added, which may be used as intensity references, for example.

Figure 5:
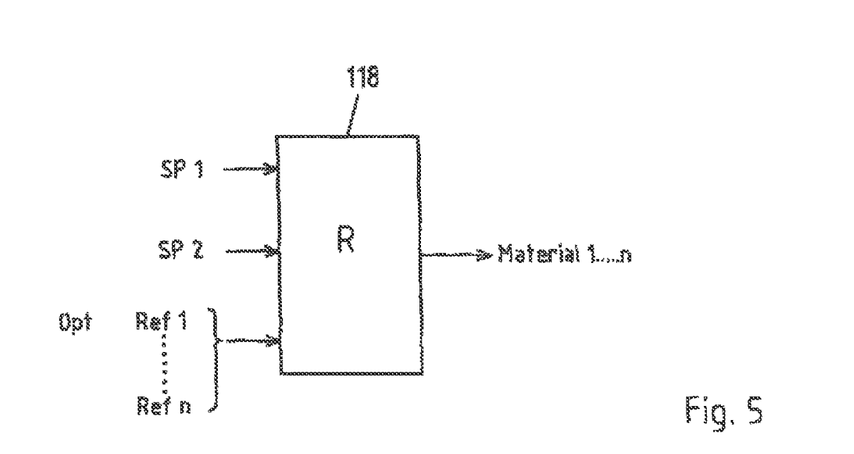
FIG. 5 shows a schematic illustration for determining materials data.

FIG. 5 illustrates a material classification system 118, which if provided with the spectral information of the spectra SP1, SP2 of FIG. 3 and the discrete spectral lines DSp3 or DSp4 of FIG. 4, will use one frame or several frames that show the test point under different aspects or at different points in time to compute a material allocation. In this, the classifier R computes a "best fit" to one of the data sets of a material sample saved in a look-up table (e.g. dental enamel or gums, or even a filling material, e.g. amalgam or gold). Subsequently the spectra SP1 and SP2 are re-computed using the data from a look-up table. For generating the data for the look-up table, known samples are measured using the system according to the invention and the spectral information SP1, SP2 and possibly additional channels, e.g. the reference channel from the live-image optics, is stored and saved as data sets in the look-up table. Preferably the data saved will already have been corrected for the Z distance value. Subsequently the measured data of an unknown material will—in a distance-corrected form—also be compared to the data sets of the look-up table, for example using the best-fit algorithm that computes least-squares for each spectral test point. To calibrate the system, spectrally resolved data of a reference body of highly diffusely scattering material is used, such as titanium oxide or Spectralon. Reference channels may be employed in an additional fashion (Ref 1 . . . Ref n). In the presence of one or several additive non-confocal reference channel(s), for example for the realization of a live image during the 3D measurements this (these) may also be employed to determine the nature of the material from the optical properties.

Figure 6:
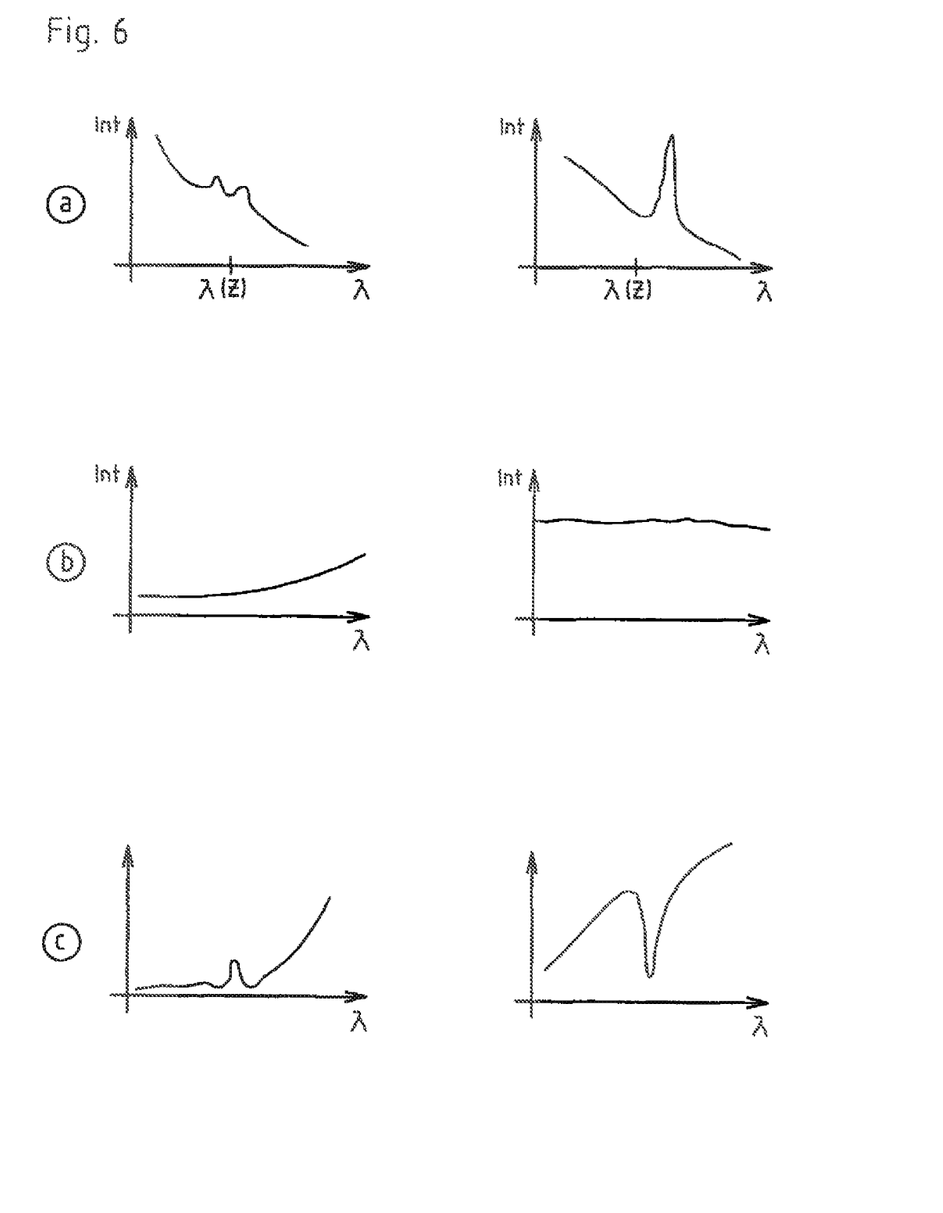
FIG. 6 shows spectra for determining correction factors.

The spectra shown in FIG. 6 will be used to illustrate how spectra are distance-correction calibrated, in order to be able to compare them with spectra saved in look-up tables, which allow inferring information about material characteristics.

FIG. 6 is used to explain the principles of a system calibration. The spectra in FIG. 6a) purely schematically represent a background spectrum (left-hand illustration) and a measured spectrum (right-hand illustration), which are recorded at a particular distance Z from a point to be measured, whereby the invention's arrangement is used that includes the pinhole array 30 with the holes 32, in which the foci are imaged, and the holes 54, that do not coincide with the illumination pattern 14. The background spectrum is measured using the radiation that passes through at least one of the holes 54. The measured spectrum is measured using a radiation that passes through one of the holes 32, which is located adjacent to one or several of the holes that are used to determine the background radiation. The measurement is performed using a test body. Evident in the right-hand illustration of FIG. 6a) is a peak for a particular wavelength, which is independent of distance (Z independent). However, in actuality the measured spectrum of the test body without the invention's confocal measuring set-up, i.e. with a pure measurement of diffuse reflection in dependence on the wavelength λ, would exhibit a shape corresponding to that shown in the right-hand illustration of FIG. 6b). As test body one uses for example Spectralon, which in the measured signal will produce a smooth straight curve, since Spectralon will reflect equally well in all wavelengths in the visible spectral regions.

Consequently a correction factor must be applied to the actual measured spectrum of the reference body (right-hand illustration of FIG. 6a)) in order to achieve a curve corresponding to that to the right-hand illustration of FIG. 6b). The correction factor (c=b:a) is represented in the right-hand illustration of FIG. 6c). By applying the correction factor, one in this manner converts the actual measured spectrum (right-hand illustration of FIG. 6a) into the spectrum of the right-hand illustration of FIG. 6b).

One consequently obtains a corrected data set, where the influence of the confocal measuring system has been compensated for.

A corresponding process applies to the background measurement results, which are represented by the left-hand spectra of FIGS. 6a), b), and c).

Corresponding spectra are measured for a multitude of distances Z between Z=0 and Z=$Z_{MAX}$, so that a complete set of spectra for various depths (distances Z) is saved and the correction factors C for each λ are computed and stored.

These correction factors subsequently can be applied to the spectra of any type of desired body (object), such as teeth, filling material, tissue, etc, so that one obtains the diffuse reflection spectra for the materials, which subsequently are compared to stored (look-up tables) test spectra, in order to perform a material classification, whereby in the comparison one uses for example the least-squares method on the test spectrum and the measured spectrum.

Since such a data set, which comprises a multitude of measurements for various distances for each test point, will contain significant levels of redundancy, it becomes possible to discard those parts of the spectra that exhibit a low signal-to-noise ratio and to use only the regions close to the peak signal.

Figure 7:
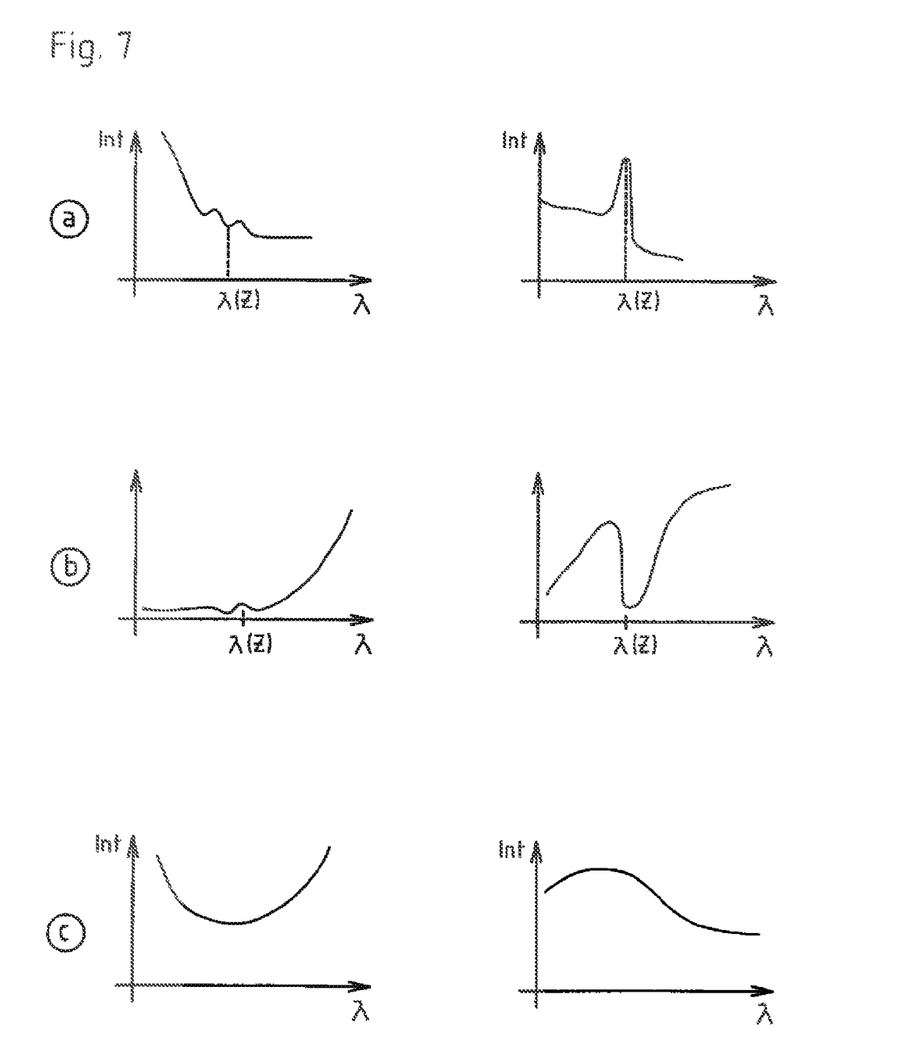
FIG. 7 shows spectra for ascertaining material characteristics of an object.

FIG. 7 shows exemplary spectra recorded from an object to be measured at a certain distance Z, in order to be able to compare the corrected spectra subsequently to stored spectra (look-up tables) and to draw conclusions with respect to the material characteristics.

For example, the right-hand illustration of FIG. 7a) shows a measured spectrum for a tooth as object. The left-hand illustration of FIG. 7a) represents the background spectrum at the same distance Z.

In accordance with the explanations for FIG. 6, corrections factors according to FIG. 6c), which correspond to the spectra 7b) are applied to the measured spectra 7a), in order to obtain corrected spectra of the tooth in accordance with FIG. 7c).

Subsequently the corresponding spectra are compared to spectra stored earlier. In accordance with the teaching of the invention, measurements of this nature will be performed for one and the same test point at various distances of the invention's measuring arrangement.

Figure 8:
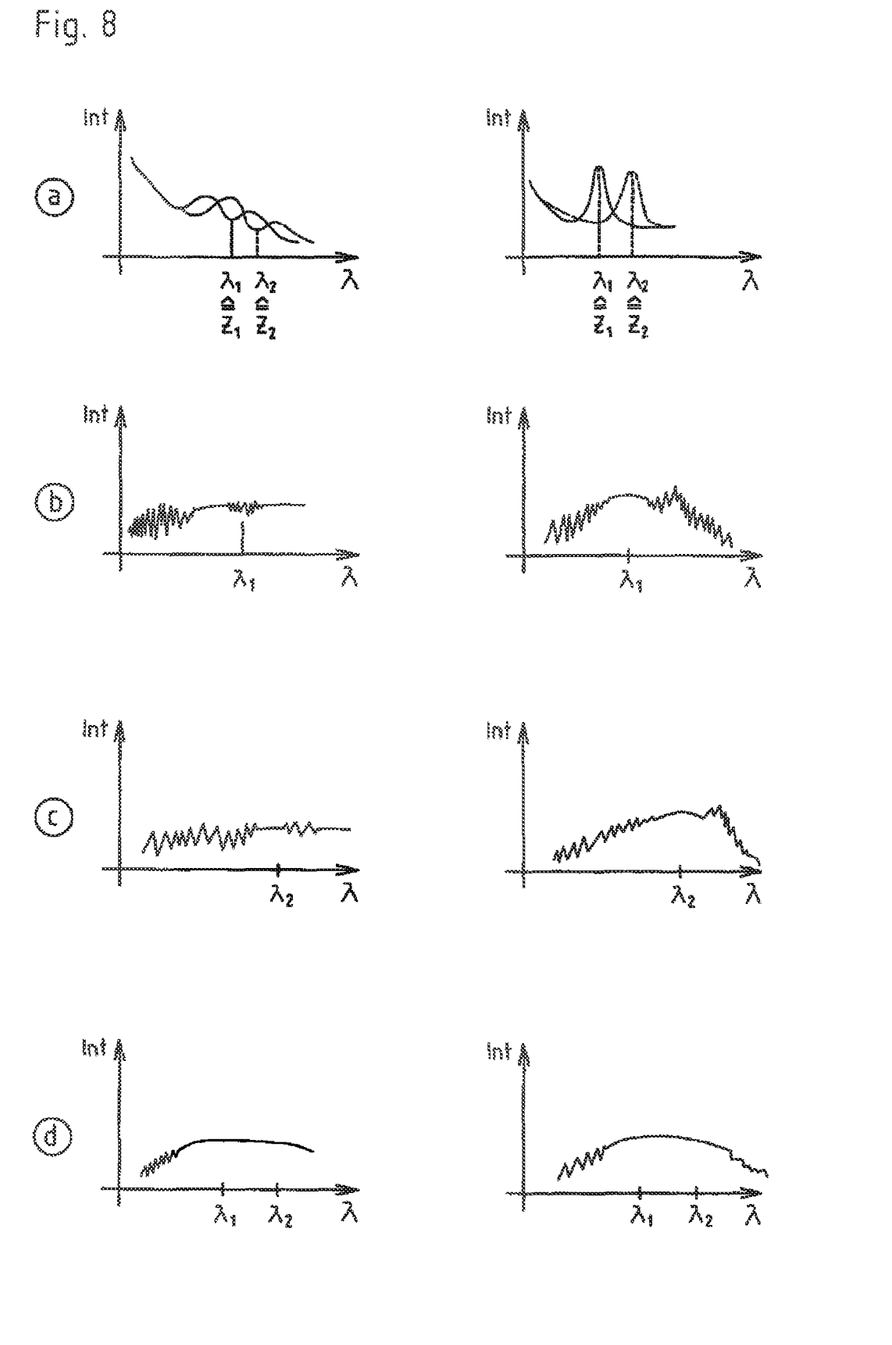
FIG. 8 shows spectra recorded with a set-up according to the invention at distances $Z_1$ and $Z_2$ from an object to be measured.

FIG. 8 is intended to illustrate the principle that the measured spectra and the background spectra change as a function of distance, since the confocal condition is met only for a particular wavelength for a particular distance and the peaks will be wavelength-dependent. This is meant to be illustrated in FIG. 8a). A first measurement curve has been measured at a distance $Z_1$ while a second measurement curve was recorded at a distance $Z_2$, whereby the peaks occur at different wavelength, $\lambda_1$ and $\lambda_2$.

FIG. 8b) shows a background measurement (left-hand illustration) and the measured spectrum (right-hand illustration) that have been corrected with respect to distance $Z_1$, whereby a correction factor was taken into account in accordance with the explanation in connection with FIG. 6. FIG. 8c) illustrates the corrected measured spectrum (right-hand illustration) i.e. the corrected background spectrum for the distance $Z_2$. Binning with respect to the adjacent wavelengths $\lambda_1$ and $\lambda_2$ achieves a noise suppression, as is illustrated in FIG. 8d).

Both the measured spectra (right-hand illustration) as well as the background spectra (left-hand illustration in the figure) can be used in a comparison to stored reference spectra (look-up table) to draw conclusions about material characteristics.

From the measured peak of the measured spectrum one may for example infer information about the surface smoothness of the object, while the background spectrum in particular provides depth information of the object, whereby due to the measurements of object points at different distances of the measuring arrangement, the material characteristics will be determined independent of wavelength.

In particular, it is possible to use the measured spectra to derive information with respect to surface roughness or smoothness, refractive index, and absorption characteristics, while the background spectra provide information about material characteristics such as scattering and absorption.

Preferably the computations are performed in real-time or nearly in real-time in an FPGA (Field Programmable Gate Array), in order not to stress the CPU of the main computer. Real-time classification is possible if the required information is contained in a single frame. However, if one would have to wait for additional frames that for example could contain a rarely occurring Fresnel reflection, the final evaluation could only take place after the arrival of this information. If the time separation is small, e.g. 30 FPS (Frames Per Second), this information will usually be available within a few seconds.

The material-related information subsequently can be displayed superimposed onto the 3D information, e.g. by differently coloured measured points in a GUI (Graphical User Interface) and/or be used for a selective treatment of the object along the lines of different materials. In case of a dental application one can determine in this manner the transition from solid tooth substance to soft tissue, cotton spacers or retraction threads. Geometrically variant parts of soft tissue may be eliminated prior to the registration of individual frames. It further becomes possible to distinguish filling materials or tooth decay from healthy tooth material. Moreover, it is possible to perform a 3D tooth colour determination including determination of the optical properties µa, µs, and g.

The invention claimed is:

1. A method of ascertaining optical properties of an object, the method comprising:

obtaining spectrally resolved data of the object from measurement data using a photodetector of a confocal three-dimensional measuring system after a first and a second radiation of the object;

wherein the first radiation is directly reflected from foci of a multi-focal illumination pattern imaged on the object;

wherein the second radiation is diffusely reflected at a distance $\Delta x$ from an imaged focus of the multifocal illumination pattern measured by the photodetector in a different position;

re-computing the measurement data of the object using spectrally resolved data of a reference body;

determining spectrally resolved data at varying distances of the confocal 3D measuring system from the object; and applying a correction factor to the spectrally resolved data, which is determined from diffuse reflection of the reference body not measured under confocal measuring conditions, or is taken from a library stored in a computer.

2. The method of claim 1, wherein a confocal colour-dispersing three-dimensional measuring system is provided.

3. The method of claim 1, wherein the distance between a directly reflected radiation assigned to a focus and a diffusely reflected second radiation is between 5 μm and 3 mm.

4. The method of claim 3, wherein the distance is between 10 μm and 200 μm.

5. The method of claim 1, wherein to determine the spectrally resolved data, the object is illuminated by means of the confocal three-dimensional measuring system with a first radiation in a wavelength region $\Delta\lambda 1$, that the object is illuminated with a second radiation in a wavelength region $\Delta\lambda 2$, and that a two-dimensional image of the object is generated from the second radiation reflected by the object.

6. The method of claim 5, wherein a three-dimensional image is measured using a first sensor of the confocal three-dimensional measuring system having first pixels to be assigned to spatial coordinates of the object and the two-dimensional image is measured with a second sensor with second pixels to be assigned to positional coordinates of the object, and that the first pixels and the second pixels are assigned to each other.

7. The method of claim 1, wherein by means of the spectral information of the spectrally resolved data determined using the first sensor and the spectral information of the spectrally resolved data determined using the second sensor, one or several frames that show a test point from different points of view and/or at different points in time, are used to compute a material classification.

8. The method of claim 1, wherein the spectra of the spectrally resolved data are compared, taking into account the correction factor, to spectra saved in look-up tables that are representative of the optical properties of the object.

9. The method of claim 1, wherein the optical properties of the object are determined from both a measured spectrum of a test point obtained under confocal conditions, as well as from a background spectrum in the region of the test point.

10. The method of claim 9, wherein spectra of the first radiation is stored in the computer as the origination of the test point.

11. The method of claim 1, wherein the distance is between 10 μm and 200 μm.

* * * * *